(12) United States Patent
Volk et al.

(10) Patent No.: US 9,763,985 B2
(45) Date of Patent: Sep. 19, 2017

(54) ANTIGEN-SPECIFIC CENTRAL-MEMORY T CELL PREPARATIONS HAVING HIGH CD4+ FRACTION

(76) Inventors: Hans-dieter Volk, Berlin (DE); Michael Schmuck, Berlin (DE); Petra Reinke, Berlin (DE)

( * ) Notice: Subject to any disclaimer, the term of this patent is extended or adjusted under 35 U.S.C. 154(b) by 250 days.

(21) Appl. No.: 14/125,101

(22) PCT Filed: Jun. 11, 2012

(86) PCT No.: PCT/EP2012/061041
§ 371 (c)(1),
(2), (4) Date: Feb. 11, 2014

(87) PCT Pub. No.: WO2012/171882
PCT Pub. Date: Dec. 20, 2012

(65) Prior Publication Data
US 2014/0154228 A1    Jun. 5, 2014

(30) Foreign Application Priority Data

Jun. 11, 2011 (EP) .................................. 11169655
Aug. 12, 2011 (EP) .................................. 11177524

(51) Int. Cl.
| | | |
|---|---|---|
| C12N 5/00 | (2006.01) | |
| C12N 5/02 | (2006.01) | |
| A61K 38/00 | (2006.01) | |
| A61K 35/26 | (2015.01) | |
| C12N 5/0783 | (2010.01) | |
| A61K 35/17 | (2015.01) | |

(52) U.S. Cl.
CPC .............. *A61K 35/26* (2013.01); *A61K 35/17* (2013.01); *C12N 5/0636* (2013.01); *C12N 2501/2302* (2013.01); *C12N 2501/2307* (2013.01); *C12N 2501/727* (2013.01)

(58) Field of Classification Search
None
See application file for complete search history.

(56) References Cited

FOREIGN PATENT DOCUMENTS

| WO | WO/2009/053109 | 4/2009 |
|---|---|---|
| WO | WO/2010/151517 | 12/2010 |

OTHER PUBLICATIONS

He et al, "Characterization of the Metabolic Phenotype of Rapamycin-Treated CD8+ T Cells with Augmented Ability to Generate Long-Lasting Memory Cells", PLoS One, vol. 6. No. 5 (May 17, 2011).

*Primary Examiner* — Michail Belyavskyi
(74) *Attorney, Agent, or Firm* — JMB Davis Ben-David

(57) ABSTRACT

The invention relates to a method for generation of T cell preparations that are specific for at least one target antigen, comprising the steps of expanding lymphoid cells in vitro in the presence of a target antigen or peptide fragments thereof in an expansion step, isolating cells that secrete interferon gamma and culturing, the cells in the presence of interleukin 2 and interleukin 7 and either an inhibitor of the mTOR Complex 1, or in the presence of an inhibitor of IL-2/IL-2R interaction. The invention further relates to preparations obtained by the method of the invention.

8 Claims, 16 Drawing Sheets

|  | | $T_{CM}$ Phenotype | Proliferation | Effector Function |
|---|---|---|---|---|
| | IL-2 | - | +++ | + |
| | IL-7 | + | - | + |
| | IL-2 / IL-7 | - | +++ | + |
| LD rapamycin or aIL-2Rα | IL-2 | + | ++ | ++ |
| | IL-7 | +++ | - | ++ |
| | IL-2 / IL-7 | +++ | +++ | +++ |

| | $T_{CM}$ Phenotype (% central-memory proportion) | Proliferation (fold expansion) | Effector Function (% IFNγ+ / TNFα+ / IL-2+ production) |
|---|---|---|---|
| - | 0-1 % | < 50 | 0-1 % |
| + | 1-5 % | 50 - 100 | 1-5 % |
| ++ | 5-10 % | 100 - 200 | 5-10 % |
| +++ | > 10 % | > 200 | > 10 % |

ANTIGEN-SPECIFIC CENTRAL-MEMORY T CELL PREPARATIONS HAVING HIGH CD4+ FRACTION

Cross-Reference to Related Applications

This is the U.S. National Stage of International Application No. PCT/EP2012/061041, filed Jun. 11, 2012, which was published in English under PCT Article 21(2), which in turn claims the benefit of European Patent Application No. 11169655.5, filed Jun. 11, 2011 and European Patent Application No. 11177524.3, filed August 12, 2011.

DESCRIPTION

The present invention relates to antigen specific CD4+ and CD8+ central-memory T cells for adoptive T cell therapy, and a method for providing such cells.

The generation of antigen-specific T-cells in vitro for the treatment of severe viral or other infections or malignancies ("adoptive therapy") aims at inducing an effective immune response against an antigen, resulting in efficient response, ideally in elimination of the infection or disease.

Adoptive cell transfer of autologous or allogeneic, ex vivo primed and expanded human cytotoxic T lymphocytes (CTLs) has emerged as a promising approach to treat both infectious and malignant diseases in humans.

T cells play a central role in controlling pathogen infections and tumors. Insufficient T-cell responsiveness is associated in particular with poor control of viruses and virus-associated tumors, but also of other pathogens and tumors. Adoptive T cell therapy is a novel promising therapeutic approach to restore immune competence.

Human cytomegalovirus (CMV) infections are a major cause of morbidity and mortality in immunocompromised individuals and may serve as an example of T-cell mediated immunity and infection control. A latent CMV infection stays clinically silent under immunocompetent situation; however, CMV causes frequent and severe complications in immunocompromised patients, such as transplant recipients. Due to the iatrogenic immunosuppression in these individuals, the formation of antigen-specific T-cell responses is very limited. A peptide-based protocol to generate ex vivo CMV-specific T-cell lines was developed (Hammer et al., Eur. J. Immunol. 2005, 35, 2250-2258). This protocol is based on short-time stimulation with peptide-pool libraries that cover almost all CD4+ and CD8+ T cell epitopes of a given protein (EP 1 257 290 B1).

He et al. (PLoS one 2011, Vol 6, e20107; WO2010/151517A2) show murine T cell preparations derived from isolated CD8+ naïve T cells primed- after isolation-in vitro by antigen peptides in the presence of isolated dendritic cells and high concentrations of rapamycin.

The clinical proof-of-concept of this approach was recently demonstrated (Brestrich et al., Am J Transplant, 2009). In vitro generated autologous CMV specific T cells were infused to a lung-transplanted patient, who suffered from severe antiviral drug resistant CMV disease and was under long-term mechanical ventilation. The adoptively transferred T cells rapidly cleared viral infection and the patient recovered within few days from ventilation that had been necessary over previous months. After full recovery, the patient was released from the clinic three weeks after T-cell infusion. After seven weeks, the patient relapsed unexpectedly. Similar data were seen with two other patients. This noticeably shows the adaptability and potential of this approach, as efficient CMV-specific T-cells were successfully generated from severely ill patients. According to the experimental data the relapse is likely due to the late differentiation phenotype of the infused T cells and therefore their insufficient longevity in vivo.

One population of cells important for the generation of immune memory are so-called "memory" cells. This population has been further divided into subpopulations, among them "CD45RA− (negative) CCR7− (negative) effector memory T cells (Tem)", and CD45RA− CCR7+ central memory (Tcm) cells. Cells belonging to the central memory subpopulation are believed to be critical to the mounting of an effective immune response upon re-encounter of antigen.

Late differentiated effector/memory T cells have powerful effector function but are not able to establish long-lasting protective memory due to diminished proliferative potential and short survival following re-challenge. In contrast, early differentiated central/memory T cells have less cytotoxic effector function but strong proliferative capacity and long lifespan. Central memory-derived effector T cells are expected show superior lasting engraftment. The persistence of transferred cells correlates with therapeutic efficacy. Balancing the engraftment fitness with strong antigen-specific effector function might lead to optimal therapeutic outcome. Hence, the objective of the present invention is to provide T-cell lines capable of strong engraftment potential after adoptive transfer. This objective is attained by the methods and preparations of the present invention.

During experiments aimed at improving engraftment and activity of adoptively transferred T cells, it was surprisingly found that partial blocking of the Interleukin 2 (IL2) receptor or modifying intracellular IL2 signaling by partial mTOR inhibition during the expansion-phase of an antigen specific T-cell line strongly increases the anti-pathogen/tumor T-cell response and, most importantly, maintains an early effector/memory cell phenotype that has been described to be associated with long-lasting efficacy in vivo.

In the present document, "CD45RA" means the human naive T lymphocyte marker (PTPRC; Uniprot ID P07585; isoform A) and CCR7 means the human chemokine receptor 7 (Uniprot ID P32248).

If any cell population is designated "positive" with respect to a certain marker protein, this designation shall mean that said cell population can be stained by a common fluorescent-dye-labelled antibody against the marker protein and will give a fluorescence signal of at least one log higher intensity compared to unlabelled cells or cells labelled with the same antibody but commonly known as not expressing said marker protein.

According to a first aspect of the invention, a method for generating T cell preparations that are specific for at least one target antigen is provided. This method comprises the following steps:

lymphoid cells are expanded in-vitro in the presence of one or more target antigens or peptide fragments thereof in an expansion step, yielding a first T cell preparation; then responding cells are isolated from the first T cell preparation in an isolation step, yielding a second T cell preparation; then in a culturing step, the cells obtained as second T cell preparation are cultured in the presence of an immune cell growth and differentiation stimulating cytokine, preferably interleukin2 and/or interleukin 7, and either an inhibitor of the mTOR Complex 1, preferably rapamycin or a rapamycin analogue such as, by way of non-limiting example, SDZ-RAD (Everolimus), or in the presence of an inhibitor of interleukin 2 (IL-2)— interleukine-2-receptor (IL-2R) interaction (such as, by way of non-limiting example, an CD25 alpha chain inhibitor such as the monoclonal antibodies referred to as basiliximab or daclizumab).

The expansion step, isolation step and culturing step proceed in the described sequence.

Responding cells in the sense of the invention are cells that secrete at least one of interferon gamma, interleukin 2 or tumor necrosis factor alpha, or cells that express CD137 or CD40L following challenge.

The T cell preparation is cultured in the presence of a cytokine, for example IL2 or IL7. Other examples are IL15 or IL21. A combination of IL2 and IL7 is preferred.

In one embodiment, responding cells are selected in the isolation step on the basis of their secretion of interferon gamma. Cells that are positive for IFN gamma secretion are included in the second T cell preparation.

In one embodiment, the target antigen is CMV, particularly immunodominant antigens pp65 or IE1 as whole peptide or as peptide libraries representing all or selected epitopes thereof.

In one embodiment, the isolation step is performed by separating cells magnetically or by flow cytometry, for example on the basis of their binding to an antibody directly or indirectly attached to a magnetic bead or fluorescent dyes. The antibody used in the examples of the present invention is bivalent and recognizes a cytokine (for example: IFN gamma, interleukin 2, tumor necrosis factor alpha) and a cell surface antigen (cytokine secretion assay), or attaches directly to the surface through activation markers CD137 or CD40L. A bivalent antibody recognizing IFN gamma and a leucocyte-specific cell surface antigen such as CD45 is preferred. The commercially available kit (IFN gamma secretion assay; Miltenyi Biotech, Bergisch Gladbach, Germany) separates the cells by selective retention in a magnetic field through an antibody attached to a magnetic bead. The antibody binds to the IFNg attached to the cell surface by the bivalent antibody.

In some embodiments, the concentration of inhibitor of the mTOR complex 1 is between 2 and 20 nmol/l. In some embodiments, the concentration of inhibitor of the mTOR complex 1 is between 10 and 20 nmol/l. In some embodiments, the concentration of inhibitor of the mTOR complex 1 is between 5 and 10 nmol/l. In some embodiments, the concentration of inhibitor of the mTOR complex 1 is between 2 and 8 nmol/l. In some embodiments, the concentration of inhibitor of the mTOR complex 1 is about 2, 4, 6, 8 or 10 nmol/l. Alternatively, an antibody inhibitor of IL-2-IL-2R interaction is used at a concentration between 2 and 20 µg/ml, preferably between 10 and 20 µg/ml.

Employing low or very low concentration of inhibitor of mTOR (e.g., rapamycin) leads to a significantly better CD4+ functionality in the resulting T cell preparation. Improved CD4+ functionality leads to improved CD4+ central memory proliferation, resulting in an overall enhanced long term T cell response including the CD8+ response. Low rapamycin concentrations also prevent overgrowing of the T cell preparation by CD8+ T cells. The preparations of the state of the art (see He et al., ibid.) emphasize the effect of high rapamycin concentrations on CD8+ short-term functionality, without taking into regard the disadvantages that are a result of CD4+ lack of function in the long term and which result from high rapamycin concentrations during culture.

In some embodiments, the inhibitor of IL-2-IL-2R interaction is a monoclonal antibody targeting the alpha chain of the IL-2R complex, CD25, particularly Daclizumab or Basiliximab.

In some embodiments, the lymphoid cells are whole blood peripheral mononuclear cells obtained from a human patient.

In some embodiments, the culturing step lasts between 10 and 25 days, particularly between 15 and 21 days, most particularly around 18 days.

According to another aspect of the invention, a T cell preparation is provided by a method according to the above aspect of the invention in any of its embodiments. This T cell preparation differs from previously reported preparations in its composition, particularly in that the cells constituting the preparation have been selected for secretion of IFN gamma, interleukin 2 or tumor necrosis factor alpha or for expression of CD137 or CD40L subsequent to antigen stimulation, and have been cultured or propagated in the presence of en mTOR or IL-2 signaling pathway inhibitor, so as to significantly skew the CD4/CD8 and central memory/effector memory T cell repertoires of the preparation in comparison to preparations obtained either in vivo, without inhibitor treatment or without prior stimulation or selection.

In some embodiments, the ratio of cells expressing CD8 to cells expressing CD4 within the preparation is smaller than (<) 6. In some embodiments, it is <5. In some embodiments, it is <4.5. In some embodiments the ratio of cells expressing CD8 to cells expressing CD4 within the preparation is around 4.

In some embodiments, the preparation is characterized by a percentage of CD45RA- and CCR7+ cells (in relation to all CD4 or CD8 positive cells of the preparation) greater than (>) 10%. In some embodiments, it is >15%. In some embodiments, the preparation is characterized by a percentage of CD45RA- and CCR7+ cells >20%.

In some embodiments, the ratio of CD4+, CCR7+ and CD45RA- (CM) cells to CD4+, CCR7- and CD45RA- (EM) cells is >3. In some embodiments, the ratio of CD8+, CCR7+ and CD45RA- (CM) cells to CD8+, CCR7- and CD45RA- (EM) cells is >1.

In some embodiments, the percentage of cells that are CD4+, CCR7+ and CD45RA- (CM/central memory cells), calculated in reference to the sum of CD4+ cells and CD8+ cells within the culture, is >15%. In some embodiments, this ratio is >20%. In some embodiments, this ration is ≥25%.

In some embodiments, the ratio (percentage) of CD8+, CCR7+ and CD45RA- (CM) cells in reference to the sum of CD4+ cells and CD8+ cells within the culture, is >5%. In some embodiments, it is >7.5%. In some embodiments, it is ≥9%.

Providing a T cell preparation with a relatively high ratio of CD4 expressing central memory cells is of great value to any application thereof, especially to treating CMV disease by adoptive transfer of the T cell preparation.

In some embodiments, a majority fraction of cells within the T cell preparation expresses CCR7, CD62L and shows prolonged CD127 expression during the first 2, 3, 4, 5 or 6 days of the culturing step.

The IFN gamma capture assay delivered CD4+ T cells representing predominantly a Tnaïve and TCM phenotype, however, the isolated CD8+ T cells showed a T(naïve), TEM and terminal differentiated memory T cell (TEMRA) phenotype. TEMRA as well as TEM secreted most IFNgamma.

In some embodiments, the preparation is characterized by having a ratio of cells expressing all of IFNγ, TNFα and IL2 of greater than (>) 10% following antigenic specific stimulation (in relation to all CD4 or CD8 positive cells of the preparation). Data are shown in FIG. 11.

Where ever embodiments are described herein in reference to details of a particular feature, or a number of features, without describing all features of the invention in last detail, such embodiments are meant to be able to be combined to render particular embodiments of the present invention. Accordingly, in one embodiment of a preparation (prepared by a method according to the first aspect of the invention) is characterized by the features that the ratio of cells expressing CD8 to cells expressing CD4 (CD8:CD4) within the preparation is smaller than (<) 6; and the ratio of CD4+, CCR7+ and CD45RA− (CM) cells to CD4+, CCR7− and CD45RA− (EM) cells is >3; and the ratio of CD8+, CCR7+ and CD45RA− (CM) cells to CD8+, CCR7− and CD45RA− (EM) cells is >1; and in relation to the sum of CD4 and CD8 positive cells of the preparation, the percentage of CD45RA− and CCR7+ cells is greater than (>) 10%, and the percentage of cells expressing all of IFNγ, TNFα and IL2 is greater than (>) 10%.

In another embodiment,
the ratio of CD8:CD4 within the preparation is <5, and
the ratio of CD4+CM cells to CD4+EM cells is >3; and
the ratio of CD8+CM cells to CD8+EM cells is >1; and
in relation to the sum of CD4 and CD8 positive cells of the preparation, the percentage of CD45RA− and CCR7+ cells is >20%, and the percentage of cells expressing all of IFNγ, TNFα and IL2 is greater than (>) 10%.

In another embodiment,
the ratio of CD8:CD4 within the preparation is <4.5, and
the ratio of CD4+CM cells to CD4+EM cells is >3; and
the ratio of CD8+CM cells to CD8+EM cells is >1; and
in relation to the sum of CD4 and CD8 positive cells of the preparation, the percentage of CD45RA− and CCR7+ cells is >20%, and the percentage of cells expressing all of IFNγ, TNFα and IL2 is greater than (>) 10%.

In another embodiment,
the ratio of CD8:CD4 within the preparation is around 4, and
the ratio of CD4+CM cells to CD4+EM cells is >3; and
the ratio of CD8+CM cells to CD8+EM cells is >1; and
in relation to the sum of CD4 and CD8 positive cells of the preparation, the percentage of CD45RA− and CCR7+ cells is >20%, and the percentage of cells expressing all of IFNγ, TNFα and IL2 is greater than (>) 10%.

In one embodiment, the cell preparation of the invention is characterized by the features that the ratio of CD8:CD4 within the preparation is <6; and
the percentage of CD45RA− and CCR7+ cells is greater than (>) 10%, and
the percentage of CD4+, CCR7+ and CD45RA− (CM) cells is >15%; and
the percentage of CD8+, CCR7+ and CD45RA− (CM) cells is >7%,
each such percentage being calculated in reference to the sum of all CD4+ cells and CD8+ cells within the preparation.

In another embodiment, the cell preparation of the invention is characterized by the features that
the ratio of CD8:CD4 within the preparation is <5, and
the percentage of CD45RA− and CCR7+ cells is >20%, and
the percentage of CD4+, CCR7+ and CD45RA− (CM) cells is >15%; and
the percentage of CD8+, CCR7+ and CD45RA− (CM) cells is >7%,
each such percentage being calculated in reference to the sum of all CD4+ cells and CD8+ cells within the preparation.

In another embodiment, the cell preparation of the invention is characterized by the features that
the ratio of CD8:CD4 within the preparation is <4.5, and
the percentage of CD45RA− and CCR7+ cells is >20%, and
the percentage of CD4+, CCR7+ and CD45RA− (CM) cells is >15%; and
the percentage of CD8+, CCR7+ and CD45RA− (CM) cells is >7%,
each such percentage being calculated in reference to the sum of all CD4+ cells and CD8+ cells within the preparation.

In another embodiment, the cell preparation of the invention is characterized by the features that
the ratio of CD8:CD4 within the preparation is around 4, and
the percentage of CD45RA− and CCR7+ cells is >20%, and
the percentage of CD4+, CCR7+ and CD45RA− (CM) cells is >15%; and
the percentage of CD8+, CCR7+ and CD45RA− (CM) cells is >7%,
each such percentage being calculated in reference to the sum of all CD4+ cells and CD8+ cells within the preparation.

The inventive T cell preparation may be used as a medicament, particularly for use in the prevention or therapy of infectious disease or cancer. The T cell preparations provided herein are of particular usefulness in patients undergoing or having undergone solid organ transplantation, especially in the prevention or therapy of infectious disease or cancer.

Although a number of tumor entities have been assigned characteristic antigens; malignant melanoma is one example. The method and composition of the instant invention will be of use for patients suffering from such tumor entities. Particular advantages are provided in virus-associated tumor indications. Epstein-Barr-Virus (EBV)-associated lymphoma, such as Post-Transplant-Lymphoproliferative Disease (PTLD) in immunocompromised patients, is a typical example. Adoptive transfer of EBV-specific T cells successfully combat PTLD in therapeutic or preemptive approaches. However, similar to CMV-specific adoptive T cell therapy, long-lasting efficacy has been observed in about 50% of transplant patients only. Phenotypic analyses revealed a dominance of late Tem phenyotype within the T-cell product as well suggesting the need for enrichment of long-lived Tcm cells to improve long-lasting effects in all patients.

A pharmaceutical composition is similarly provided, comprising a T cell preparation according to any of the above described embodiments and a pharmaceutically acceptable carrier, excipient, medium or diluent, for use in the prevention or therapy of infectious disease or cancer.

Similarly, a method of treatment of infectious disease or cancer is provided, comprising the preparation and administration of a T cell preparation according to the invention, to a patient in need thereof.

The impressive effects described in the Figures and Examples demonstrate the utility of partially blocking the IL2 receptor by a receptor alpha chain antagonist during the expansion-phase of the culture, which strongly increases antiviral T-cell responses and maintains an early effector/memory phenotype without significantly affecting clonal expansion. Modifying IL2 signaling by intracellular mTOR (mammalian target of Rapamycin, Gene ID: 2475) inhibition resulted in comparable outcome, identifying partial modification of the IL2 signaling to be responsible for this effect. Hence, either intracellular IL2 signaling modification or partial inhibition of extracellular binding of the ligand (blocking one of the three receptor units) leads to this effect. The quality and durability of CD4-mediated antiviral CD8+ T-cell responses were significantly enhanced. The agent-dose for Sirolimus (Rapamycin), as model substance of a mTOR inhibitor, must not exceed 20 nM, otherwise the effect is opposed. Concentration of Daclizumab (Simulect), as model substance of IL-2 receptor antagonist, must not exceed 20 µg/mL. Clinical grade materials have been established; hence autologous TCM generation is an achievable clinical-grade approach. Both sirolimus and IL2-receptor antagonist are approved for clinical use (immunosuppression), making their usage possible. Titration experiments with high/normal drug dosage used in clinic were performed, showing the immunosuppressive properties where T cell growing was fully inhibited. The treated T-cell lines show statistically significant prolonged expression of the cell surface markers CD127, CCR7 and CD62L, which characterize a specific phenotype of central/memory cells. One specific feature of central/memory T cells is the ability to secrete high amounts of IL2 following antigen stimulation. In vivo this is crucial for their autocrine activation resulting in proliferation. Compared to the untreated specimen, the generated T-cell lines show among effector cytokine secretion, significantly higher IL2 secretion after stimulation. In this experimental setting, Daclizumab as well as Sirolimus enhance the quantity and quality of virus-specific T cells in vitro. The generated T-cell lines showed dose-dependent specific lysis of peptide loaded targets and enhanced cytokine secretion. Notably, the inhibition significantly balanced the CD4/CD8 ratio, what consecutively leads to a superior antiviral CD8 response in vitro. Daclizumab as well as Sirolimus treatment increased the CD4+ T cell proportion in the culture, resulting in strong antigen-specific CD8+ T cell effector response. Of note, treated CMV specific T cells show no differences in specific target lysis, excluding a negative influence of the drugs on functionality. This study reveals a potent strategy to generate antigen-specific T cells with a high functional capacity and maybe robust long-term persistence in vivo.

As defined in here, the term "rapamycin" defines a class of immunosuppressive compounds which contain the basic rapamycin nucleus characterized by a formula I.

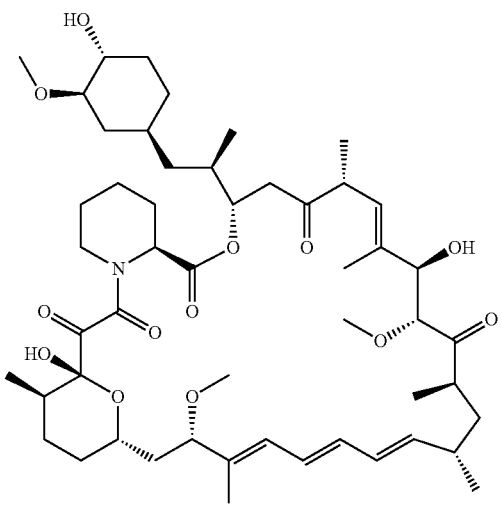

The rapamycins of this invention include compounds, which may be chemically or biologically modified as derivatives of the rapamycin nucleus, while still retaining immunosuppressive properties.

Accordingly, the term "rapamycin" includes esters, ethers, oximes, hydrazones and hydroxylamines of rapamycin, as well as rapamycins in which functional groups of the rapamycin have been modified, for example through reduction or oxidation. The term "rapamycin" also includes pharmaceutical acceptable salts of rapamycins, which are capable of forming such salts, either by virtue of containing an acidic of basic moiety.

It is preferred that the esters and ethers of rapamycin are of the hydroxyl groups at the 42- and/or 31-position of the rapamycin nucleus, esters and ether of a hydroxyl group at 27-position (following chemical reduction of the 27-ketone), and that the oximes, hydrazones, and hydroxylamines are of a ketone at the 42 position (following oxidation of the 42-hydroxyl group) and of 27-ketone of the rapamycin nucleus.

Preferred 42- and/or 31-esters and ethers of rapamycin are disclosed in the following patents, which are all hereby incorporated by reference: alkyl esters (U.S. Pat. No. 4,316,885); aminoalkyl esters (U.S. Pat. No. 4,650,803); fluorinated esters (U.S. Pat. No. 5,100,883); aminoesters (U.S. Pat. No. 5,130,307); aminodiesters (U.S. Pat. No. 5,162,333); amino alkanoic esters (U.S. Pat. No. 5,389,639); amide esters (U.S. Pat. No. 5,118,677); silyl esters (U.S. Pat. No. 5,120,842); actetals (U.S. Pat. No. 5,51,413); sulfonate and sulfate esters (U.S. Pat. No. 5,177,203); esters (U.S. Pat. No. 5,221,670); alkoxyesters (U.S. Pat. No. 5,233,036), O-aryl, -alkyl, -alkenyl and alkynyl ethers (U.S. Pat. No. 5,258;3899, carbonate esters (U.S. Pat. No. 5,260,300); arylcarbonyl and alkoxycarbonyl carbamates (U.S. Pat. No. 5,262,423); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); phosphorylcarbamate esters (U.S. Pat. No. 5,391,730); amidino carbamate esters (U.S. Pat. No. 5,463,048); carbamates (U.S. Pat. No. 5,302,584); carbamate esters (U.S. Pat. No. 5,411,967; U.S. Pat. No. 5,434,260; U.S. Pat. No. 5,480,988; U.S. Pat. No. 5,480,989; U.S. Pat. No. 5,489,680; U.S. Pat. No. 5,118,678); hindered N-oxide esters (U.S. Pat. No. 5,491,231), biotin esters (U.S. Pat. No.

5,504,091); O-alkyl ethers (U.S. Pat. No. 5,665,772); and PEG esters of rapamycin (U.S. Pat. No. 5,780,462). The preparation of these compounds is disclosed in the patents listed above.

Accordingly, examples of rapamycin include compounds characterized by general formula II

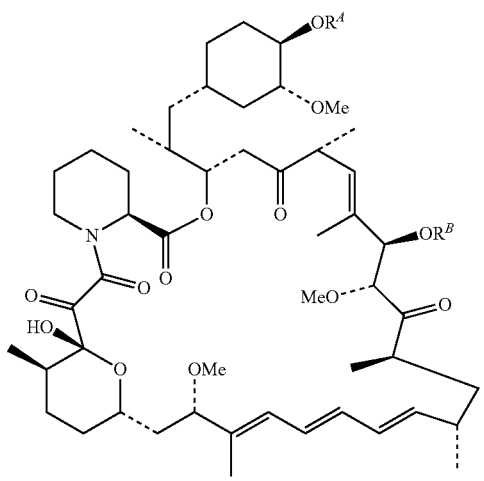

(II)

wherein $R^A$ and $R^B$ are each selected from hydrogen and esters of ethers forming groups disclosed in any one of the abovementioned patents.

Preferred 27-esters and ethers of rapamycin are disclosed in U.S. Pat. No. 5,256,790, which is hereby incorporated by reference. The preparation of these esters and ethers is disclosed in the aforementioned patent.

Preferred oximes, hydrazones and hydroxylamines of rapamycin are disclosed in U.S. Pat. No. 5,373,014, U.S. Pat. No. 5,378,836, U.S. Pat. No. 5,023,264 and U.S. Pat. No. 5,563,145, which are hereby incorporated by reference. The preparation of these oximes, hydrazones and hydroxylamines are disclosed in the above listed patents. The preparation of 42-oxorapamycin is disclosed in U.S. Pat. No. 5,023,263, which is hereby incorporated by reference.

Particularly preferred rapamycins include rapamycin (U.S. Pat. No. 3,929,992) rapamycin 42-ester with 3-hydroxy-2-(hydroxymethyl)-2-methylpropionic acid (U.S. Pat. No. 5,362,718) and 42-O-(2-hydroxyl)ethyl rapamycin (U.S. Pat. No. 5,665,772).

When applied, pharmaceutical acceptable salts can be formed from organic and inorganic acids, for example, acetic, propionic, lactic, citric, tartaric, succinic, fumaric, maleic, malonic, mandelic, malic, phtalic, hydrochloric, hydrobromic, phosphoric, nitric, sulfuric, methanesulfonic, naphtalensulfonic, benzenesulfonic, toluenesulfonic, camphorsulfonic and similarly known acceptable acid when the rapamycin contains a suitable basic moiety. Salts may also be formed from organic and inorganic bases such as alkali metals salts (for example sodium, lithium or potassium), alkali earth metal salts, ammonium salts, alkylammonium salts, containing 1 to 6 carbon atoms or dialkylammonium salts containing 1 to 6 carbon atoms in each alkyl group and trialkylammonium salts containing 1 to 6 carbon atoms in each alkyl group, when rapamycin contains a suitable acidic moiety.

Preferred inhibitors of mTOR are:
Sirolimus (CAS number 53123-88-9), also known as rapamycin,
Everolimus (III a; CAS number 159351-69-6), which is a 40-O-(2-hydroxylethyl) derivative of rapamycin.
Temsirolimus (IIIb; CAS number 162635-04-3)

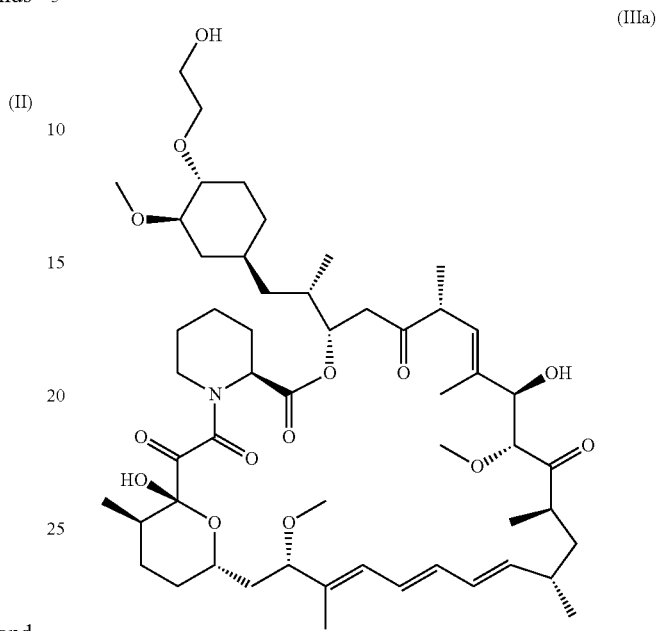

(IIIa)

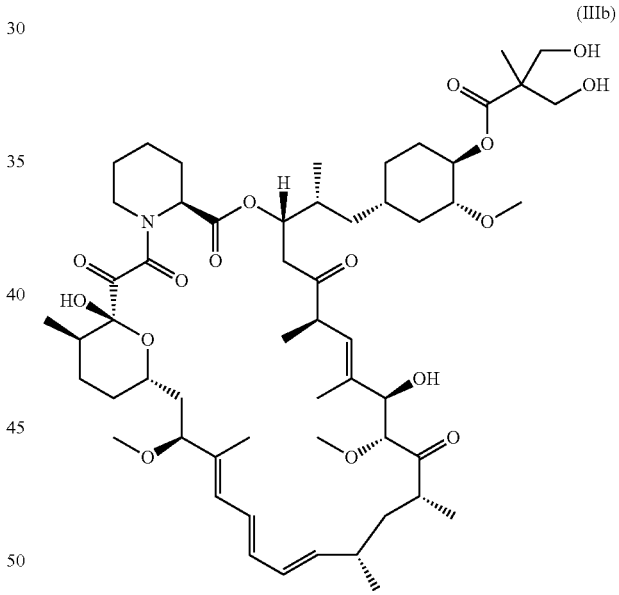

(IIIb)

Preferred antibodies to inhibit the alpha chain of IL2-receptor complex (Gene ID: 3559) are:
Daclizumab (CAS number 152923-59-3), a humanized monoclonal antibody,
Basiliximab, (DrugBank entry DB00074), a chimeric mouse-human monoclonal antibody.
Gene ID numbers in this document refer to entries in the Gene data base of the United States National Center for Biotechnology Information.

EXAMPLES

Experimental Setup
Protocols for expansion and selection follow the techniques published in WO2009/053109.

CMV-specific T-cells were enriched and expanded using a previously described technique (Becker et al., Nat. Med. 2001, 7, 1159-62). Briefly, $4 \times 10^7$ autologous PBMCs were stimulated for 6 h with 1 µg/mL overlapping human cytomegalovirus phosphoprotein 65 (pp65) and immediately early 1 protein (IE1) peptide pools (JPT Peptide Technologies). Pools consisted of 15-mer peptides overlapping by 10 amino acids and were dissolved in dimethyl sulfoxide (DMSO). IFNγ producing cells underwent positive selection by the IFNγ capture-system (Miltenyi Biotech) according to the protocol provided by the manufacturer. IFNγ+ cells were next cultured for 18 days in 24-well plates together with $10^7$ irradiated autologous PBMCs using RPMI 1640 supplemented with 10% fetal bovine serum 1% Penicillin/Streptomycin (Biochrom) and 50 U/mL rIL2 (Chiron) and 10 ng/mL rIL7 (Cellgenix) or solitary when indicated elsewise. Where indicated, either mTor-inhibitor (sirolimus, Sigma-Aldrich) at very low dose (VLD, 2 nM) and low dose (LD, 20 nM) or IL2 receptor antagonist (Basiliximab, Simulect, Novartis) at 20 µg/mL were added from day 1 on every two days together with subsequent media supplementation.

Assessment of Cytotoxic Activity

Differentiated monocytes infected with CMV-related laboratory wildtype strain NEWT were used as targets. To mimic CMV-infection, autologous LCL were pulsed with 1 µg/mL overlapping CMVpp65/IE-1 peptide pools, whereas unpulsed LCL display uninfected targets. Targets were labeled with 10 µM carboxyfluorescein succinimidyl ester (CFDA-SE Molecular Probes). As controls, unpulsed LCL and uninfected differentiated monocytes (Fibroblast incubated) were labeled with 5 µM dimethyldodecylamine oxide-succinimidyl ester (Far Red; Invitrogen). Cells were co-cultured for 16 h in T cell/target ratio of 10:1. Probes were analyzed as triplicates using LSR-II flow cytometer. Samples without T cells, containing only APC (pulsed/NEWT or unpulsed) displayed internal control. Analysis was gated on live/dead-discrimination staining-dye negative cells (near-IR fluorescent reactive dye, Invitrogen). The mean percent survival of pulsed or NEWT infected targets was calculated relative to antigen-unpulsed controls. Percentaged lytic activity of target lysis was calculated as follows: mean percent survival of targets in cultures containing defined numbers of effector T cells in comparison to control cells without T cells. See also I. F. Hermans et al., Journal of immunological methods 285, 25 (Feb. 1, 2004)

Intracellular Cytokine Staining

Following antigen specific stimulation, cytokine secretion (IFNγ, TNFα and IL2) and activation marker expression (CD137 and CD154) were determined by intracellular fluorescence staining. All antibodies were purchased from Becton Dickinson (BD), except indicated. Virus infected monocytes and peptide-pool loaded LCL or monocytes (1 µg/mL IE-1/pp65) were added to T cells in diluting ratio of 1:10. Unpulsed LCL or monocytes (DMSO incubated) display unstimulated control. For effector cytokine detection, cultured T cells were re-stimulated for 18 h in the presence of 1 µg/mL brefeldin A (Sigma-Aldrich). For CD107a (H4A3) detection, 2 µM monensin (Golgi Stop, BD) was ancillary added. Cells were then harvested and phenotype was stained with monoclonal antibodies for surface markers CD3 (UCHT1, eBioscience), CD8 (3B5, Invitrogen) and CD4 (SK3). To define memory phenotypes, T cells were extracellularly stained for CCR7 (#150503, R&D), CD62L (DREG56, Beckman Coulter), CD45RA (2H4LDH11LDB9, Beckman Coulter) and CD127 (hIL-7R-M21). To exclude dead cells, live/dead-discrimination staining-dye (Invitrogen) was added. Subsequently, cells were permeabilized with Perm2 solution (BD Biosciences) and stained for IFNγ (4S.B3, eBiosciences), TNFα (MAb11), IL2 (MQ1-17H12), CD137 (4B4-1) and CD154 (TRAP1). To define regulatory T cells, T cells were stained intranuclear for Foxp3 (259D/C7) and Helios (22F6, BioLegend). For intracellular staining of Foxp3 and Helios, Foxp3 staining kit from eBioscience was used. Cells were measured with a LSR-II flow cytometer and analyzed using FlowJo Version 8 software (Tree Star). Lymphocytes were gated based on the FSC versus SSC profile and subsequently gated on FSC (height) versus FSC to exclude doublets.

Flow Cytometric Analysis

Following antigen specific stimulation, cytokine secretion (IFNγ, TNFα and IL2) and activation marker expression (CD137 and CD154) were determined by intracellular fluorescence staining. All antibodies were purchased from Becton Dickinson (BD), except indicated. Virus infected monocytes and peptide-pool loaded LCL or monocytes (1 µg/mL IE-1/pp65) were added to T cells in diluting ratio of 1:10. Unpulsed LCL or monocytes (DMSO incubated) display unstimulated control. For effector cytokine detection, cultured T cells were re-stimulated for 18 h in the presence of 1 µg/mL brefeldin A (Sigma-Aldrich). For CD107a (H4A3) detection, 2 µM monensin (Golgi Stop, BD) was ancillary added. Cells were then harvested and phenotype was stained with monoclonal antibodies for surface markers CD3 (UCHT1, eBioscience), CD8 (3B5, Invitrogen) and CD4 (SK3). To define memory phenotypes, T cells were extracellularly stained for CCR7 (#150503, R&D), CD62L (DREG56, Beckman Coulter), CD45RA (2H4LDH11LDB9, Beckman Coulter) and CD127 (hIL-7R-M21). To exclude dead cells, live/dead-discrimination staining-dye (Invitrogen) was added. Subsequently, cells were permeabilized with Perm2 solution (BD Biosciences) and stained for IFNγ (4S.B3, eBiosciences), TNFα (MAb11), IL2 (MQ1-17H12), CD137 (4B4-1) and CD154 (TRAP1). To define regulatory T cells, T cells were stained intranuclear for Foxp3 (259D/C7) and Helios (22F6, BioLegend). For intracellular staining of Foxp3 and Helios, Foxp3 staining kit from eBioscience was used. Cells were measured with a LSR-II flow cytometer and analyzed using FlowJo Version 8 software (Tree Star). Lymphocytes were gated based on the FSC versus SSC profile and subsequently gated on FSC (height) versus FSC to exclude doublets.

Other antigens or epitopes to which the current invention is applicable include, by way of non-limiting example, antigens of Ebstein Barr virus (EBV), human papillomavirus (HPV), human immunodeficiency virus (HIV), or tumour-associated antigens such as WT1, PAX2/8, Tyrosinase, and/or MAGE.

Hence, the present invention shall not be limited to CMV-specific T-cells but is rather directed towards a general method of providing pathogen-specific cell preparations for use in medicine.

SHORT DESCRIPTION OF THE FIGURES

Figure 4:
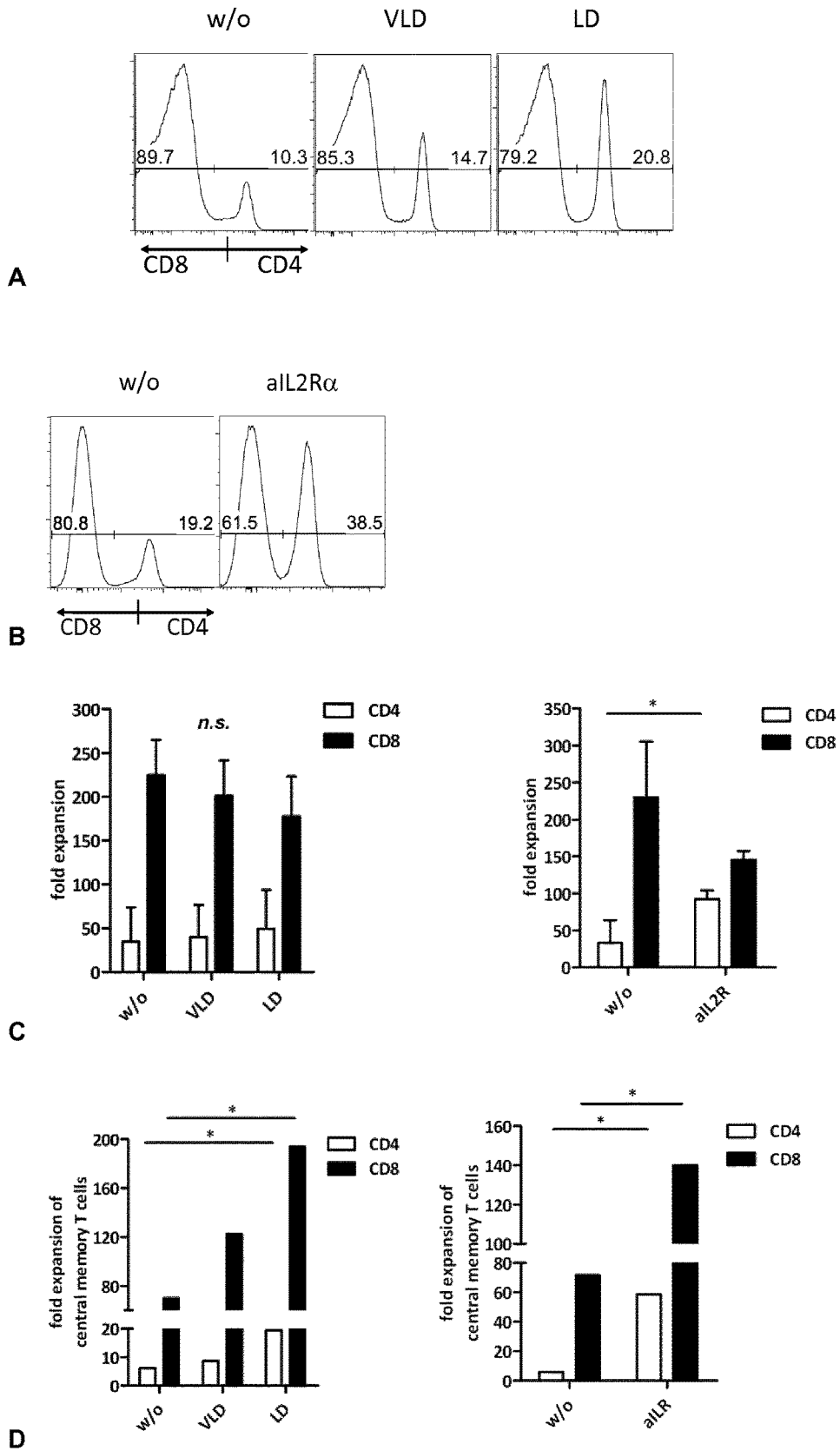

FIG. 4 shows a cytometric assessment of the expression of CD4+ and CD8+ in T cells after 18d expansion under the indicated treatment (A; VLD, LD =Sirolimus (rapamycin); B; aIL2R=IL2-receptor antagonist) and the expansion factors of total culture (C) and TCM (D) after 18 d of treatment.

Figure 5:
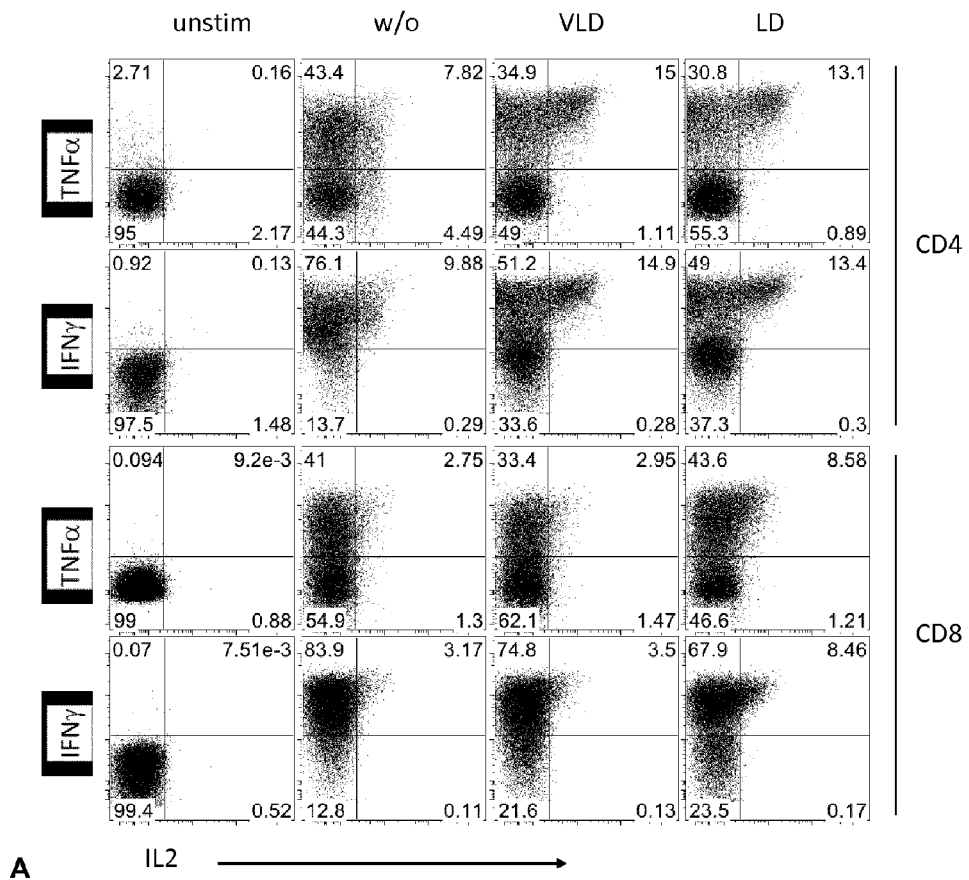
Figure 5:
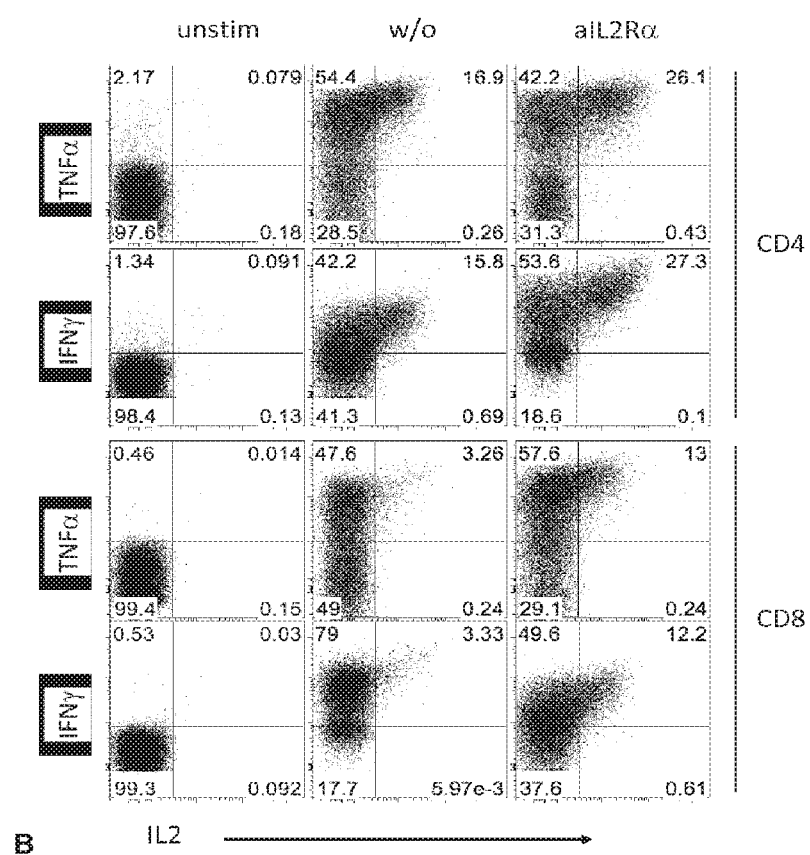

FIG. 5 (A Sirolimus, B aIL2R) shows the functional characterization of CMV-specific expanded T cells on day 18 (A; VLD, LD=Sirolimus (rapamycin), B; aIL2R=IL2-receptor antagonist; unstim: unstimulated controls).

Figure 6:
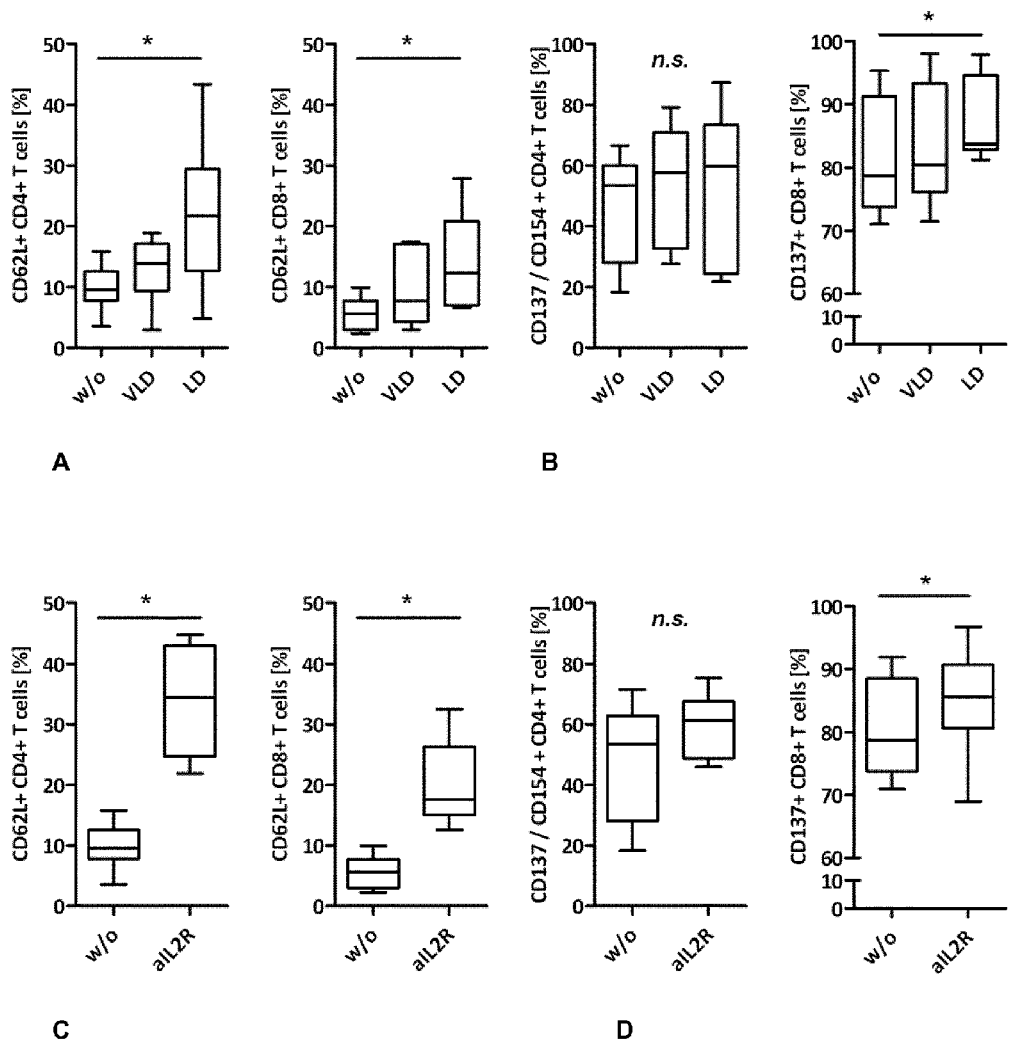

FIG. 6 (A, B: sirolimus; C, D: aIL2R) shows the phenotypic characterization (A, C: left panel; CD4+ CD62L+/and right panel; CD8+ CD62L+ expression and B, D: activation marker expression; left panel; CD4+ CD137+ CD154+ and right panel; CD8+ CD137+) of CMV-specific expanded T cells on day 18. All percentages relate to total (sum of) CD4 and CD8 cells.

Figure 7:
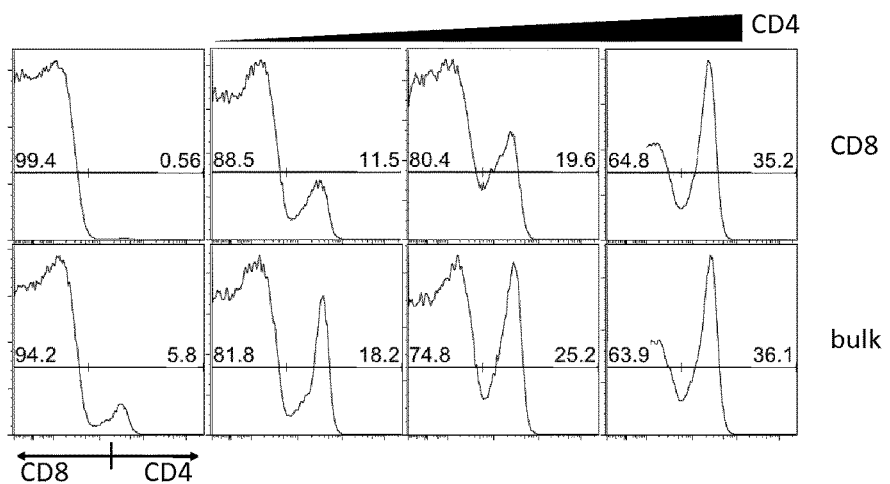
Figure 7:
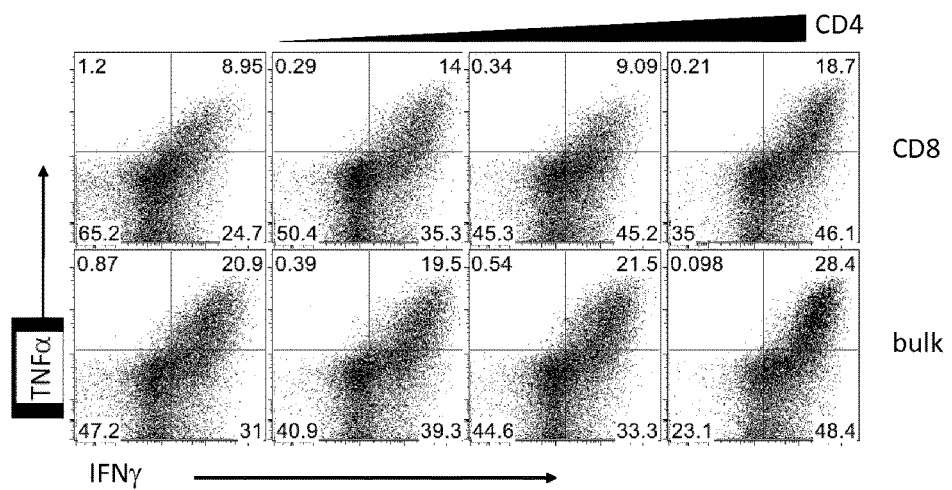
Figure 7:
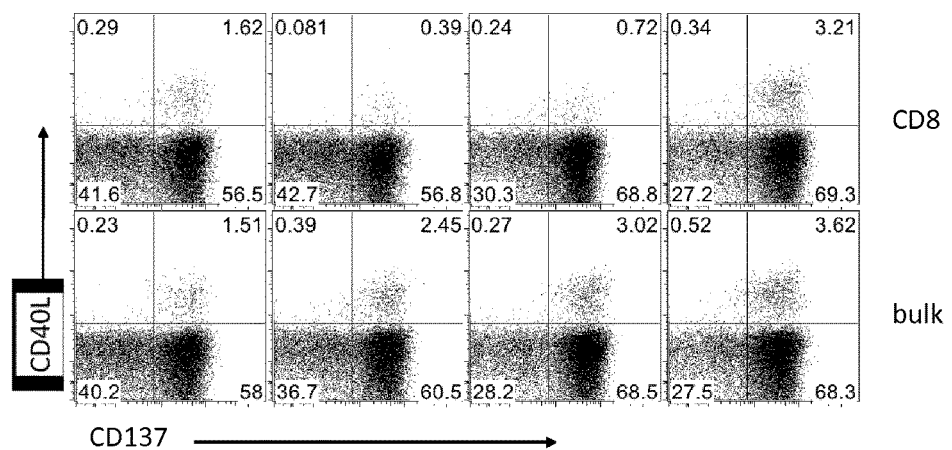

FIG. 7 Bulk culture (both, CD4+ and CD8+), single CD4+ and single CD8+ T cells were separately cultured for 18 days. (A) Histoplots indicate CD4+ T-cell amount in the respective specimen. Analysis of CD8+ T cells (upper panel) and CD8+ T cells of the bulk culture (lower panel) was performed without further addition of CD4+ T cells and gradient supplementation of CD4+ T cells prior specific re-stimulation (crescendo bar denotes increasing CD4+ T cell amount). (B) IFNγ and TNFα cytokine secretion and (C) CD137 and CD154 activation marker expression were determined by intracellular staining. Shown is functionality of CD8+ T-cell (upper panel) and CD8+ T-cells within bulk culture (lower panel) modified by gradient supplementation of CD4+ T cells.

Figure 8:
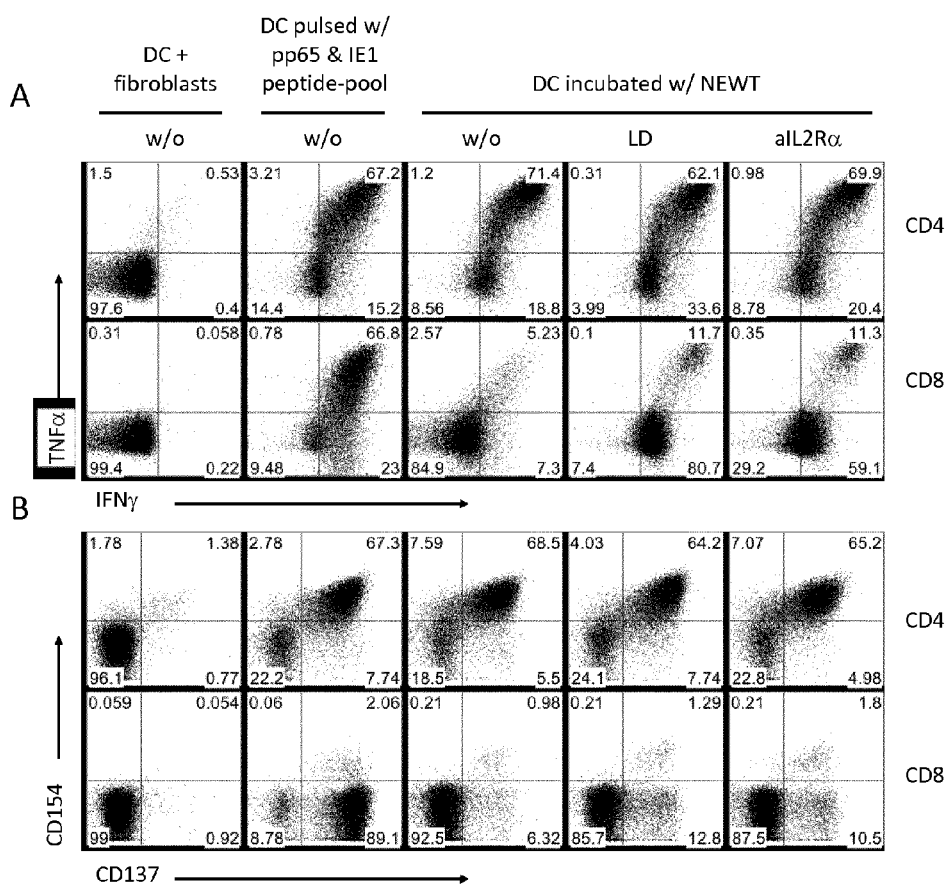

FIG. 8 Modifying IL2-receptor signaling by targeting IL-2 receptor binding or mTor pathway enables superior protective CD4-mediated CD8+ T-cell immunity. Fig. shows the capacity of CMV peptide-pool specific T cells expanded with either sirolimus or IL2-receptor antagonist to superiorly respond to NEWT infected autologous monocytes. Following specific stimulation, IFNγ and TNFα cytokine secretion (upper panel) and CD137 and CD154 (lower panel) activation marker expression were determined by intracellular staining.

Figure 9:
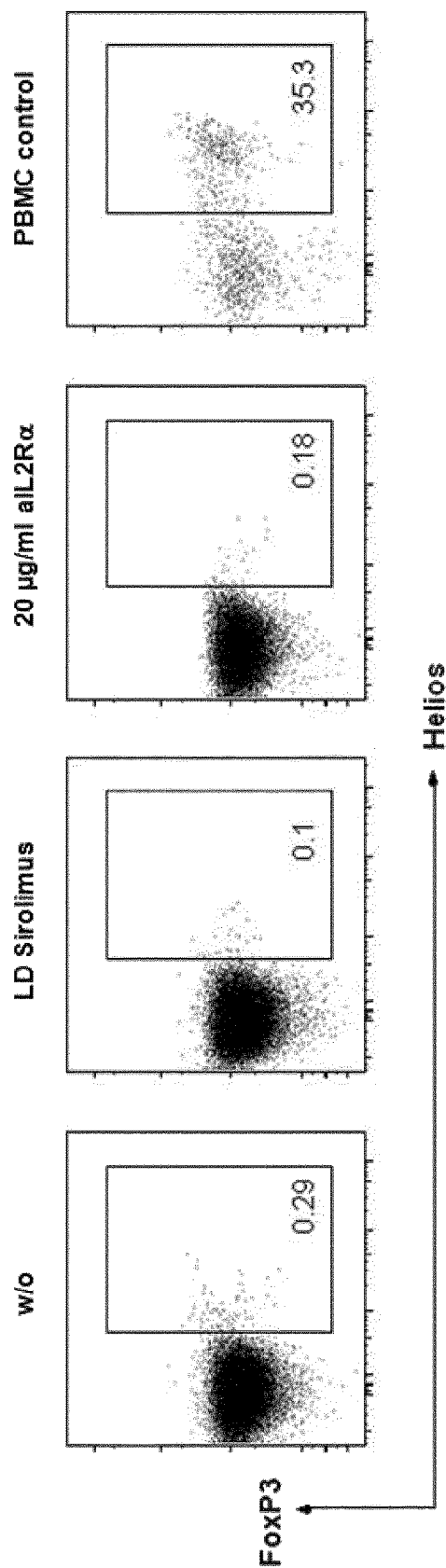

FIG. 9 shows the cytometric measurement to assess regulatory T cells with the specific markers FoxP3 and Helios.

Figure 10:
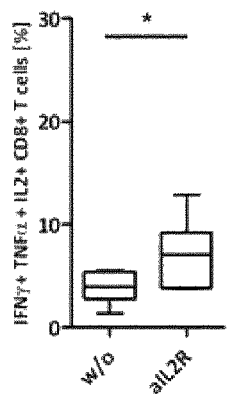
Figure 10:
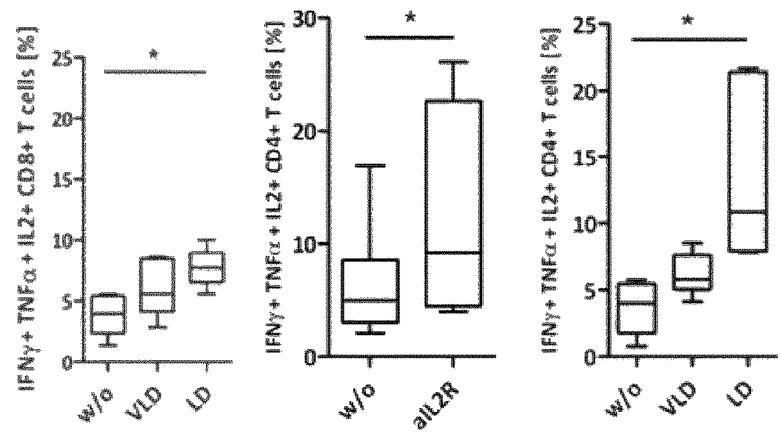

FIG. 10 shows a summary of six independent experiments showing polyfunctional (IFNγ+, TNFα+, IL2+) antigen specific T-cell responses against CMVpp65/IE1 peptide-pool pulsed LCL. Respective inhibitor treatment is indicated. Frequencies were assessed by flow cytometry.

Figure 11:
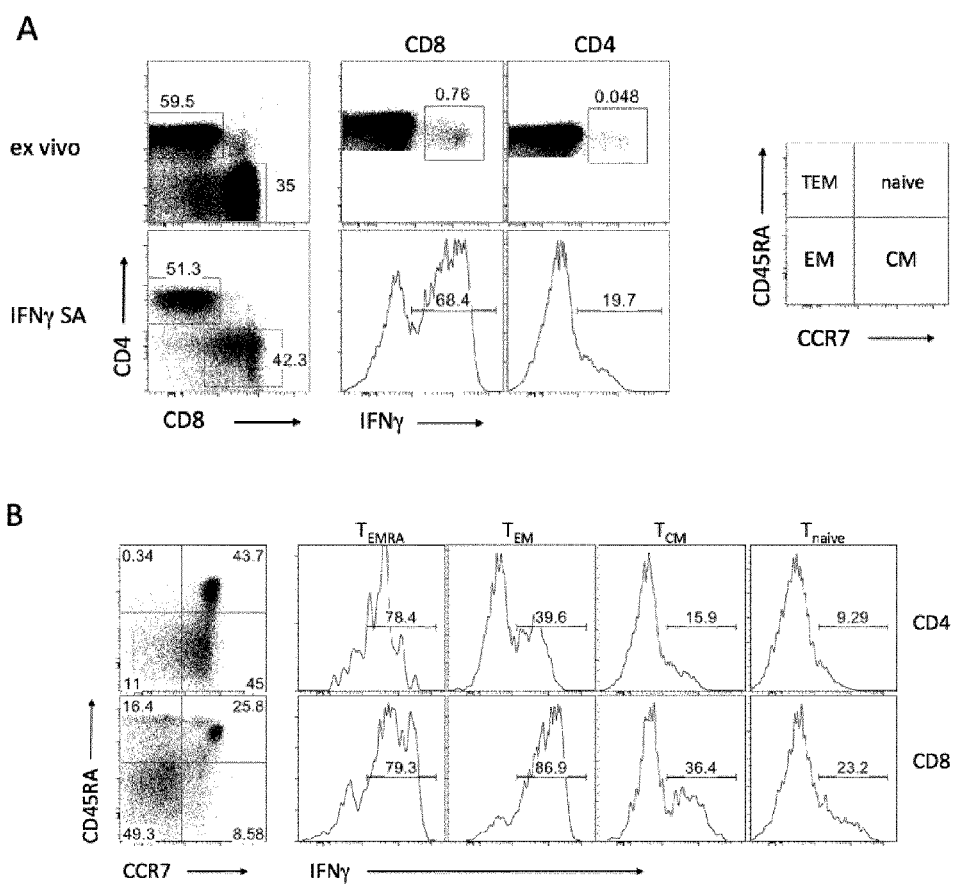

FIG. 11 shows the IFNg T-cell response following ex vivo CMV-peptide stimulation and the frequencies and purities of the IFNg capture assay for CD4+ and CD8+ T cells, respectively.

Figure 12:
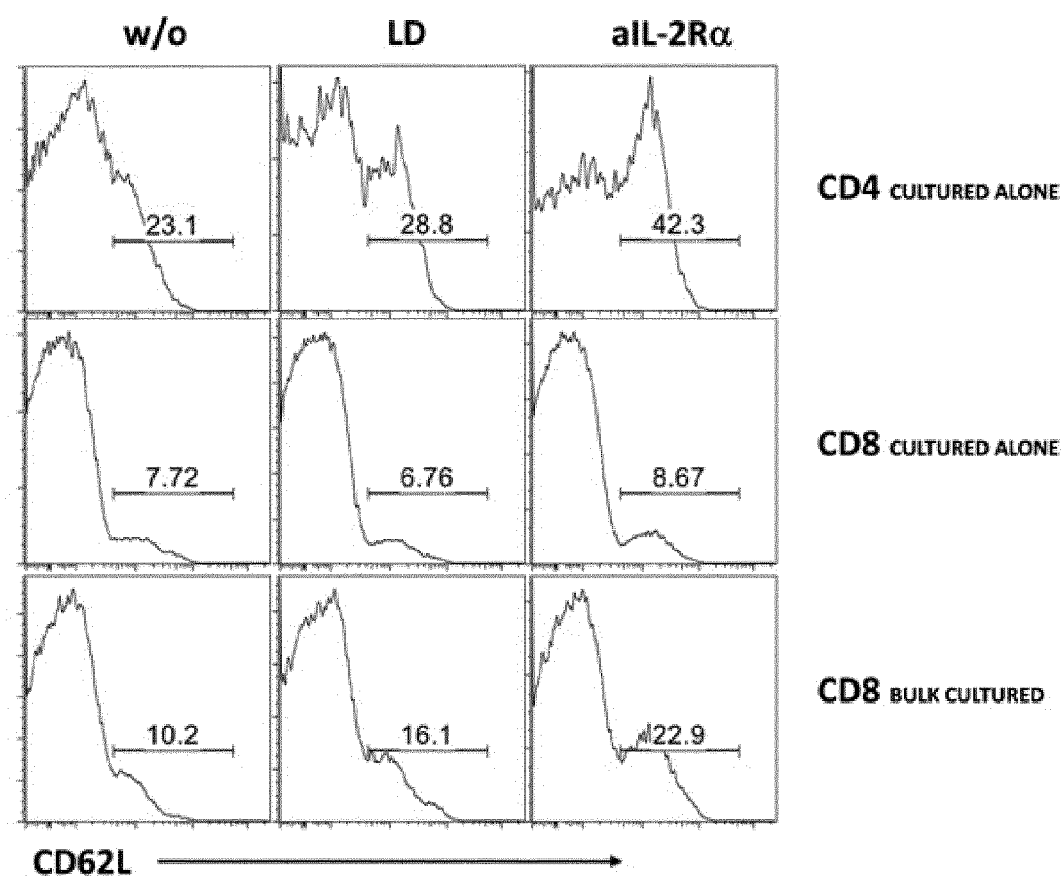

FIG. 12 shows a cytometric assessment the CD62L expression on CD4+ T cells and CD8+ T cells. CD4+ T cell help improves antiviral CD8+ T cell response. Targeting IL-2 signaling preserved CD62L expression on expanded CMV-specific CD4+ T cells. Isolated CMV-specific CD4+/CD8+ T cells were cultured separately with rapamycin (LD) or aIL-2Ra. In all plots, one representative of three experiments is shown.

FIG. 13 shows the growth factor dependency of in vitro generated $T_{CM}$ cells. CMV-specific T cell lines were generated as described. Summary of four independent experiments showing differentiation, proliferation, and effector function of all possible permutations of the variables: IL-2, IL-7, rapamycin (LD), and IL-2R antagonist (aIL-2Rα).

Figure 14:
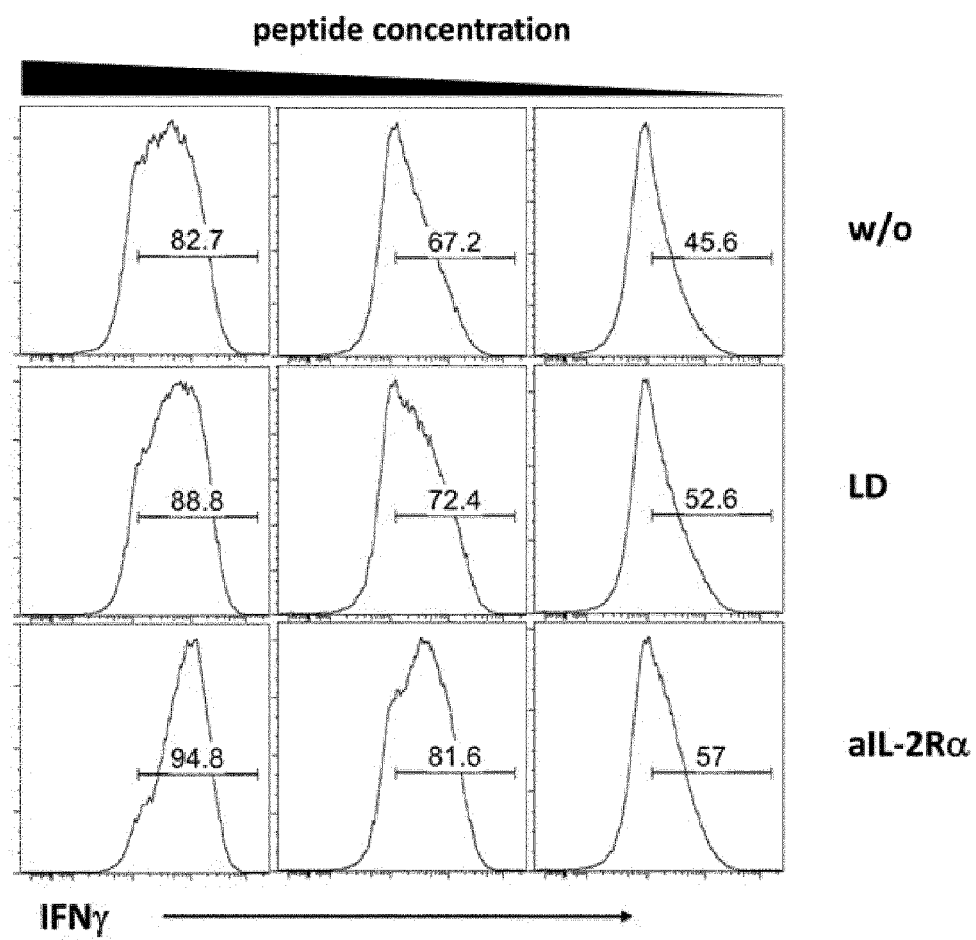

FIG. 14 shows the IFNγ secretion of IL-2R targeted cultures in dependence to the concentration of CMVpp65/IE1 peptides. IL-2R pathway-targeted cultures exhibit enhanced T cell recognition. T cells were restimulated for 18 h with peptide loaded autologous LCL at declining peptide concentrations of 1, 0.1, or 0.01 mg/ml pp65/IE-1 (crescendo bar denotes increasing peptide concentrations). IFNg cytokine secretion was determined by intracellular staining. In all plots, one representative of three experiments is shown.

Figure 15:
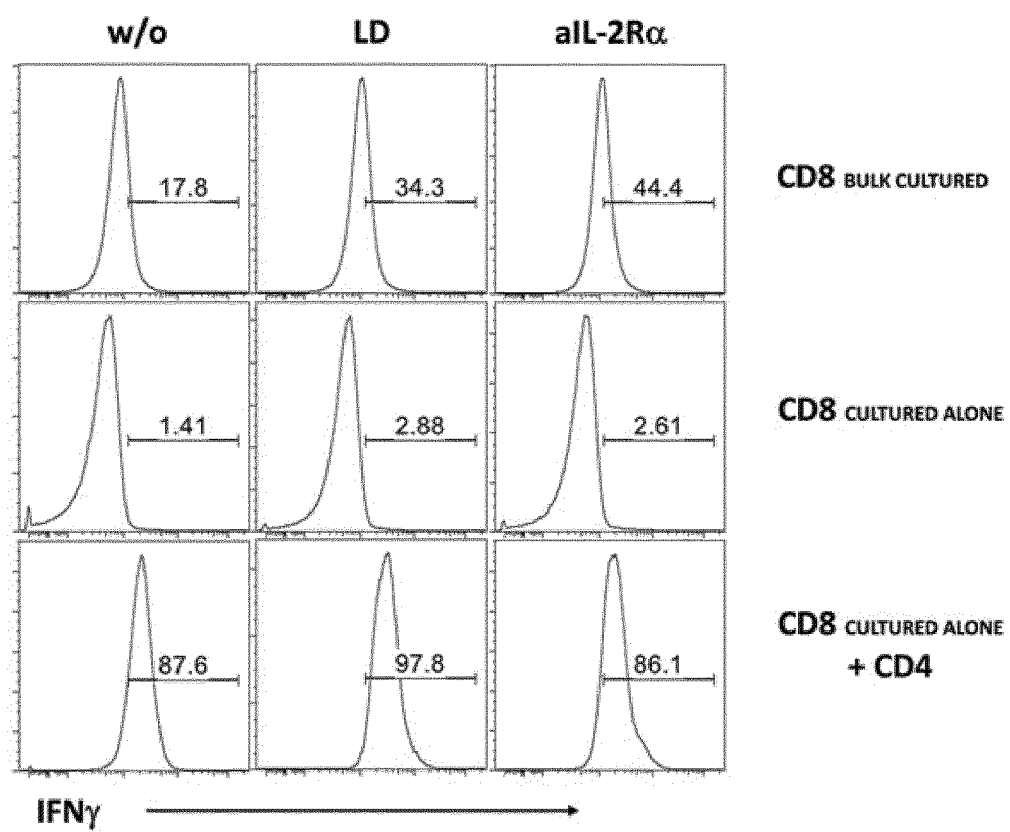

FIG. 15 shows the IFNγ secretion of CD8+ T cells within bulk culture or of CD8+ T cells that were cultured alone. CD8+ T cell function can be induced by supplementing equal numbers of CD4+ T cells just before specific restimulation. Shown is IFN-g secretion of CD8+ T cells within bulk culture or IFN-g secretion of CD8+ T cells that were cultured alone. CD8+ T cells were cultured separately with rapamycin (LD) or aIL-2Rα, as indicated.

DETAILED DESCRIPTION OF THE FIGURES

Figure 1:
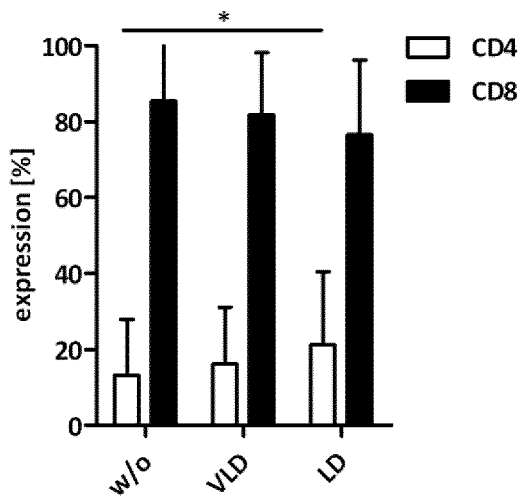
FIG. 1 shows the CD4+ and CD8+ expression (A) and the proportion of central memory T cells within CD4+ (left panel) and CD8+ (right panel) (B) of CMV antigen-specific T cells after 18 days of expansion in the presence of rapamycin (VLD=2 nM, LD=20 nM; Sirolimus (rapamycin)).
Figure 1:
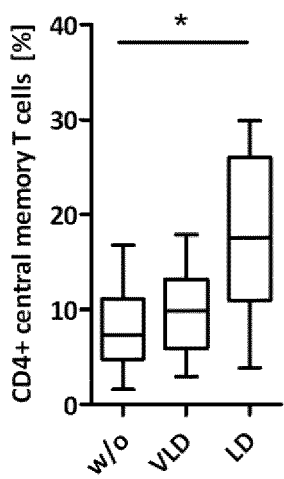
Figure 1:
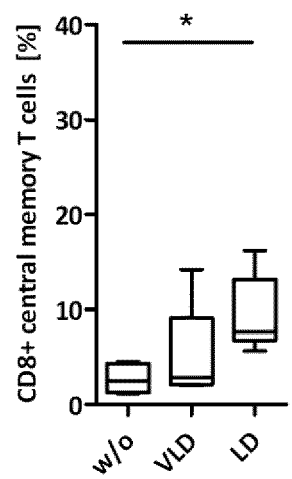

As shown in FIG. 1A, the method of the invention leads to a more balanced CD4+/CD8+ T cell ratio after 18 days of expansion without affecting clonal expansion. Low doses (LD; 20 nmol/l) or very low doses (VLD; 2 nmol/l) Sirolimus (Rapamycin) was supplemented every 2 days of culture during 14-18 days.

As shown in FIG. 1B, the differentiation phenotype after 18 days of expansion with Sirolimus significantly increases central/memory T cells. Prolonged central/memory phenotype was defined by cellsurface protein staining for CCR7 and CD45RA. Central / memory T cells are characterized by CCR7—but no CD45RA expression. LD and VLD meanings as above.

Figure 2:
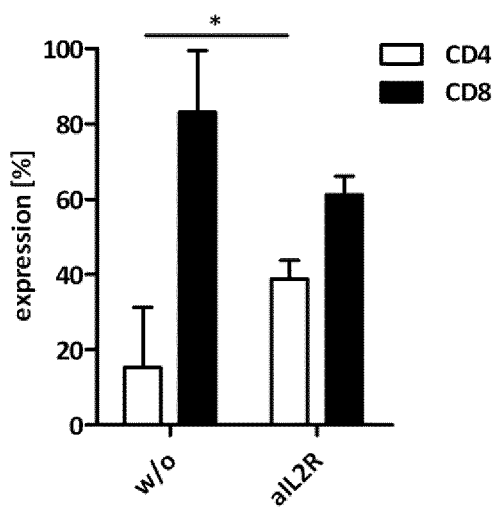
FIG. 2 shows the CD4+ and CD8+ expression (A), and the proportion of central memory T cells within CD4+ (left panel) and CD8+ (right panel) (B) of CMV antigen-specific T cells after 18 days of expansion in the presence of aIL2R (aIL2R=IL2-receptor antagonist).
Figure 2:
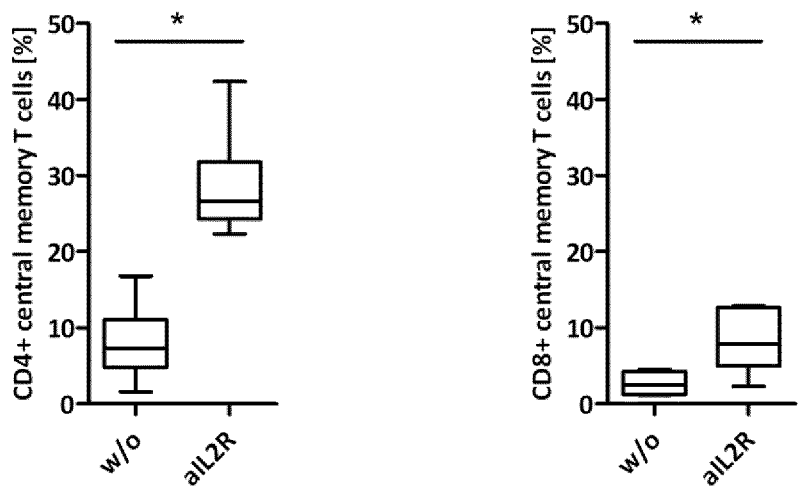

FIG. 2A shows the prolonged central/memory phenotype in aIL2R treated specimen. Similarly to treatment with mTor inhibitor (rapamycin), IL2R interference leads to a more balanced CD4+/CD8+ T cell ratio after 18 days of expansion. aIL2R (20 µg/mL) was supplemented every 2 days of culture. As shown in FIG. 2B, the differentiation phenotype after 18 days of expansion with aIL2R antagonist significantly increases central memory T cells. Prolonged central/memory phenotype was defined by cellsurface protein staining for CCR7 and CD45RA. Central/memory T cells are characterized by CCR7—but no CD45RA expression. LD and VLD meanings as above.

Figure 3:
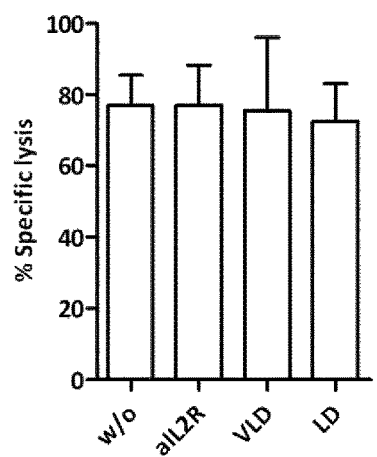
FIG. 3 shows specific target lysis of treated CMV specific T cells.

FIG. 3 demonstrates that treated CMV specific T cells show no differences in specific target lysis. Target lysis was defined by flow-cytometric vitality assay. The data demonstrate that treated CMV specific T cells show no differences in specific target lysis. Target lysis was defined by flow-cytometric vitality assay.

FIG. 4 shows that modifying IL2 signaling by partial mTOR/IL2Ra inhibition leads to an increased CD4 proportion in antigen-stimulated and IFNgamma-selected T cells after 18d expansion under the indicated treatment (FIG. 4 A;B). Cells were stained for live/dead dye, CD3, CD4 and CD8. Fig C shows summarized fold expansion CD4 and CD8 T cells after indicated treatment. Fold expansion was reduced, clonal expansion of total culture was not significantly affected. Fig. D shows that rapamycin or aIL2R antagonist treatment leads to sequential expansion of both CD4 and CD8 central memory T cells.

FIG. 5 shows the cytometric assessment of the cytokine secretion and activation marker expression of CD4+ and CD8+ T cells (A Sirolimus; B aIL2R antagonist). Frequencies were assessed following antigen specific stimulation. Specific T-cells were stimulated for 18 h (16 h Brefeldin A) w/peptide loaded APCs in ratio of 1:10. APCs were pulsed with 1 µg/mL IE-1/pp65 peptide pool. IFNγ, TNFα and IL2 cytokine secretion and CD137 and CD154 activation marker expression were determined by intracellular staining. Cells were permeabilized and stained for IFNγ, IL2, TNFα, live/dead dye, CD3, CD4, CD8, CD137 and CD154.

FIG. 6 shows the cytometric assessment of the differentiation phenotype of CD4+ and CD8+ T cells after 18 d expansion and indicated treatment (A, B Sirolimus; C, D aIL2R antagonist). Cells were stained for live/dead dye, CD3, CD4, CD8, CD45RA, CD62L and CCR7. Sirolimus or aIL2R treated CMV specific T-cell lines showed significant prolonged expression of the cell surface marker CD62L. Sirolimus or aIL2R treated CMV specific CD8+ T cells showed dose-dependent elevated CD137 activation marker expression. However, CD137 and CD154 activation marker expression on CD4+ T cells was not impaired after sirolimus treatment. Wilcoxon signed rank test with two-tailed p value, *=p<0.05. Box plots with median and interquartile range. Data are pooled from six independent experiments.

FIG. 7 shows the antiviral CD8 response in dependence of the presence of CD4+ cells in the preparation. Figure shows the cytometric assessment of activation marker CD137 expression and intracellular cytokine staining on CD8+ T cells. Frequencies were assessed following antigen specific stimulation. Specific T-cells were stimulated for 18 h (16 h Brefeldin A) w/CMVpp65/IE1 peptide-pool pulsed APCs in ratio of 1:10. CD8+ T cells and CD4+ T cells were stimulated in co-culture for 18 h at declining CD8+ T cells/CD4+ T cells ratios. Cells were permeabilized and stained for CD137 and CD154 activation marker expression and cytokines (TNFα, IFNg). Cells were stained for Live/dead dye, CD3, CD4, CD8, CD137 and CD154.

FIG. 8 shows the the capacity of CMV peptide-pool specific T cells expanded with either sirolimus or IL2-receptor antagonist to superiorly respond to NEWT infected autologous monocytes. Specific T-cell lines were generated as described. Targets (monocytes) incubated with the CMV low-passage-number clinical strain NEWT were used as APC. Target cells and T cells were co-cultured for 18 h in T cell/target ratio of 10:1. CD137 and CD154 activation marker expression and cytokine secretion capacity were determined by intracellular staining. After 2 h Bref-A was added for cytokine detection. Cells were permeabilized and stained for live/dead dye, CD3, CD4, CD8, IFNg, TNFa, CD137 and CD154. Fibroblast incubated monocytes respresent unstimulated controls.

FIG. 9 shows the cytometric assessment of regulatory T cell specific markers FoxP3 and Helios. Natural regulatory T cells are not found in CD4+ and CD8+ T cells after 18d expansion and indicated treatment.

FIG. 10 mTor inhibition or aIL2R blocking during the T-cell expansion phase augments polyfunctional antigen specific T-cell responses. Cells were stimulated for 18 h (16 h Brefeldin A) with CMVpp65/IE1 peptide-pool pulsed LCL in ratio 10:1. Cells were permeabilized and stained for IFNγ, TNFα, IL2, live/dead dye, CD3, CD4, and CD8. Summary of six independent experiments showing polyfunctional (IFNγ+, TNFα+, IL2+) antigen specific T-cell responses against CMVpp65/IE1 peptide-pool pulsed LCL. Statistical significance was calculated with Wilcoxon matched pairs test. *p<0.05.

FIG. 11 shows the IFNg T-cell response following ex vivo CMV-peptide stimulation and the frequencies and purities of the IFNg capture assay for CD4+ and CD8+ T cells, respectively. Compared to CD4+ T cells, CD8+ T cells produced substantial higher amounts of IFNg. According to CCR7 and CD45RA expression, human memory T cells can be segregated into Tnaïve cells, terminal differentiated effector cells (TEMRA), TCM and TEM. The IFNg capture assay revealed CD4+ T cells representing predominantly a Tnaïve and TCM phenotype, however, the isolated CD8+ T cells showed a Tnaïve, TEM and TEMRA phenotype (FIG. 11B). The large Tnaïve cell proportion in both, CD4+ and CD8+ T cells have to be considered as assay contamination. As shown in FIG. 11B TEMRA as well as TEM secreted most IFNg.

As shown in FIG. 12, isolated CMV-specific CD4+ and CD8+ T cells were separately cultured with rapamycin/IL-2Rα antagonist. Rapamycin/IL-2Ra antagonist-incubated CD8+ T cell bulk cultures as well as IL-2R pathway-targeted CD4+ T cells showed increased CD62L expression. In contrast, CD62L expression on purified CD8+ T cells could not be enhanced. Hence, CD8+ T cell effector function and memory phenotype in antigen-specific T-cell cultures can be improved in the presence of CD4+ T cells.

As shown in FIG. 13, T cells expanded with IL-2 alone showed strong proliferation and good cytokine secretion capacity; however, the majority of the T cells displayed a late differentiated TEM phenotype. IL-7 alone showed remarkably reduced T-cell proliferation but somewhat preserved CCR7/CD62L expression compared to supplementation with IL-2 or IL-2/IL-7. Addition of rapamycin/IL-2Ra antagonist together with either IL-2 or IL-7 promotes TCM formation by maintaining cytotoxicity. In presence of rapamycin/anti-CD25 mAb, IL-2 alone was less effective in preserving the TCM phenotype but much more potent in the expansion and inducing effector functionality compared to IL-7 alone. The best results regarding the expansion rate and keeping the TCM phenotype with full functionality were seen after cultivation with both, IL-2 and IL-7, in the presence of rapamycin/IL-2Ra antagonist.

As shown in FIG. 14, the T-cells were stimulated with decreasing peptide-concentrations to define the range of T-cell recognition. The IFNg T-cell response dropped proportionally with declining peptide concentrations. Compared to T cells derived from IL-2R pathway-targeted cultures, untreated T cells showed stronger reduction in IFNg cytokine secretion at declining peptide concentrations. The living infection model requires an effective T-cell recognition since the presentation of epitopes is reduced compared to peptide loaded cells.

To test the impact of the CD4+ T cell quantity on CD 8+ cell function in this infection model, CMV-specific T cells from PBMC were isolated and cultured in parallel bulk T cells, sorted CD4+ and CD8+ T cells, as shown in FIG. 15. Following specific re-stimulation with NEWT-infected iDC, CD8+ T cells cultured in bulk showed marginally IFNg effector cytokine secretion, whereas CD8+ T cells cultured in bulk derived from IL-2R pathway-targeted cultures revealed a much higher response. CD8+ T cell cultured without CD4+ T cells showed almost abolished IFNg cytokine secretion. Of note, CD8+ T-cell functionality, defined by IFNg secretion, could be enhanced by supplementing equal numbers of CD4+ T cells just before specific re-stimulation.

The invention claimed is:

1. A method for generation of a mixed CD4+ and CD8+ central memory T cell preparation that is specific for at least one target antigen, comprising the steps of:
   expanding lymphoid cells in vitro in the presence of a target antigen or peptide fragments thereof in an expansion step, yielding a first T cell preparation, wherein the lymphoid cells are isolated from whole blood peripheral mononuclear cells obtained from a human patient;
   isolating responding cells from the first T cell preparation in an isolation step, yielding a second T cell preparation;
   culturing, in a culturing step, the cells obtained as second T cell preparation in the presence of a cytokine, preferably interleukin 2 and/or interleukin 7, and
      i. an inhibitor of the mTOR Complex 1, preferably rapamycin or a rapamycin analogue, wherein the concentration of the inhibitor of the mTOR complex 1 is between 2 nmol/l and 20 nmol/l, or
      ii. an inhibitor of interleukin 2 (IL-2)—interleukin-2-receptor (IL-2R) interaction
   thereby generating a mixed CD4+ and CD8+ central memory T cell preparation that is specific for at least one target antigen.

2. The method according to claim 1, wherein the concentration of inhibitor of IL-2-IL-2R interaction is between 2 to 20 µg/ml.

3. The method according to claim 1, wherein the inhibitor of IL-2-IL-2R interaction is a monoclonal antibody targeting CD25, particularly Daclizumab or Basiliximab.

4. The method according to claim 1, wherein the culturing step lasts between 10 and 25 days, between 15 and 21 days, or about 18 days.

5. A method for generation of a mixed CD4+ and CD8+ central memory T cell preparation that is specific for at least one target antigen, comprising the steps of:
   expanding lymphoid cells in vitro in the presence of a target antigen or peptide fragments thereof in an expansion step, yielding a first T cell preparation, wherein the lymphoid cells are isolated from whole blood peripheral mononuclear cells obtained from a human patient;
   isolating responding cells from the first T cell preparation in an isolation step, yielding a second T cell preparation;
   culturing, in a culturing step, the cells obtained as second T cell preparation in the presence of a cytokine, preferably interleukin 2 and/or interleukin 7, and an inhibitor of interleukin 2 (IL-2)—interleukin-2-receptor (IL-2R) interaction thereby generating a mixed CD4+ and CD8+ central memory T cell preparation that is specific for at least one target antigen.

6. The method according to claim 1, wherein the concentration of the inhibitor of IL-2-IL-2R interaction is between 2 to 20 µg/ml.

7. The method according to claim 1, wherein the inhibitor of IL-2-IL-2R interaction is a monoclonal antibody targeting CD25, particularly Daclizumab or Basiliximab.

8. The method according to claim 1, wherein the culturing step lasts between 10 and 25 days, between 15 and 21 days, or about 18 days.

\* \* \* \* \*